(12) United States Patent
Victor et al.

(10) Patent No.: US 7,463,157 B2
(45) Date of Patent: Dec. 9, 2008

(54) METHOD AND SYSTEM FOR RECOGNIZING DRIVER IMPAIRMENT

(75) Inventors: Trent Victor, Göteborg (SE); Petter Larsson, Ytterby (SE)

(73) Assignee: Volvo Technology Corp., Gothenburg (SE)

( * ) Notice: Subject to any disclaimer, the term of this patent is extended or adjusted under 35 U.S.C. 154(b) by 107 days.

(21) Appl. No.: 11/420,864

(22) Filed: May 30, 2006

(65) Prior Publication Data

US 2007/0008151 A1  Jan. 11, 2007

Related U.S. Application Data

(63) Continuation of application No. PCT/EP03/13480, filed on Nov. 30, 2003.

(51) Int. Cl.
*G08B 23/00* (2006.01)

(52) U.S. Cl. .......... 340/576; 340/573.1; 340/439; 340/575; 180/272

(58) Field of Classification Search ........ 340/439, 340/575, 573.1, 576, 425.5; 180/272, 270, 180/269, 282; 280/735, 734, 736; 600/372, 600/390, 503; 701/1, 301
See application file for complete search history.

(56) References Cited

U.S. PATENT DOCUMENTS 5,465,079 A * 11/1995 Bouchard et al. .......... 340/576
5,691,693 A    11/1997 Kithil
5,900,819 A *  5/1999 Kyrtsos .................... 340/576
6,061,610 A *  5/2000 Boer ........................ 701/1
6,130,617 A   10/2000 Yeo
6,265,978 B1 * 7/2001 Atlas ........................ 340/575

FOREIGN PATENT DOCUMENTS

| FR | 2794354 A | 12/2000 |
|---|---|---|
| GB | 2284582 A | 6/1995 |
| JP | 62-061830 | 3/1987 |
| JP | 10-272959 | 10/1998 |
| JP | 2000-020897 | 1/2000 |
| JP | 2003-099899 | 4/2003 |
| WO | 1997/39920 | 10/1997 |
| WO | 2000/50261 A2 | 8/2000 |
| WO | 0237932 A | 5/2002 |

OTHER PUBLICATIONS

International Search Report from corresponding International Application No. PCT/EP2003/013480.
International Preliminary Examination Report from corresponding International Application No. PCT/EP2003/013480.
Japanese Official Action (including translation) from corresponding Japanese Application 2005-510871.

* cited by examiner

*Primary Examiner*—Anh V La
(74) *Attorney, Agent, or Firm*—WRB-IP LLP

(57) ABSTRACT

A method and system for recognizing and/or detecting impairment and/or inattention of a person, especially a driver of a vehicle, and especially caused by drowsiness, distraction and/or workload, is disclosed by detecting and evaluating head movements of the person and/or head movement reactions of the person upon a disturbance exerted onto the vehicle.

32 Claims, 5 Drawing Sheets

METHOD AND SYSTEM FOR RECOGNIZING DRIVER IMPAIRMENT

The invention relates to a method and system for recognizing and/or detecting impairment and/or inattention of a person, especially a driver of a vehicle, and especially caused by drowsiness, distraction and/or workload, by detecting and evaluating head movements of the person.

The vast majority of traffic accidents—about 90% according to an American study primary cause of collisions, accounting for an estimated 25-55% of crashes (according to an NHTSA study of the CDS database representing over 2,5 million towaway crashes per year—Wang, et al, 1996). Substantially, at least one of the following three components contribute to driver inattention: drowsiness, distraction and/or workload. Common crash types and locations caused by inattention are rearend crashes, crashes at intersections, at lane change/merge locations, at road departures, as well as single vehicle crashes or crashes on low speed limit roadways.

More in detail, collisions caused by drowsiness are a very serious road safety problem. 57% of drivers who have been asked, reported that they have driven while being drowsy and 23% the that they had actually fallen asleep while driving (Johnson, 1998). Drivers cannot reliably tell when they are impaired by fatigue to the point of having a serious vigilance lapse or uncontrolled sleep attack (Wylie, et al, 1996; Brown, 1997). Low vigilance and later stages of drowsiness impairs alertness and judgment, and hence driving performance (Williamson et al, Fatigue has been estimated to be involved in between 2% and 23% of all crashes (Knipling & Wang, 1995). These crashes occur more often late at night or in mid-afternoon. They typically involve a single vehicle drifting out of the lane or road at high speeds with no indications that the driver attempted to avoid this (NHTSA, 1998). The injuries in case of a crash are often very serious. Sleepy drivers are also often involved in rear-end and head-on collisions (op.cit.). These statistics are most likely underestimates of the real problem since drivers tend to be unwilling to recognize or admit that sleepiness was a factor in causing their crash (Stutts, Wilkens & Vaughn, 1999).

Furthermore, drivers often attend to things that are not related to driving. These things are often called secondary tasks and are potential reasons for distraction. Unfortunately, the driver is often unaware of the effects that distraction has on the driving task (Boase, et al, 1988; Stern, et al, 1996). As a result, distraction (including visual distraction and mental distraction, i.e., looking without seeing) is found to account for at least 22.9% of crashes (Wang, et al, 1996). Since 1996 there has been a rapid increase and market penetration of new information systems and that may be used within the vehicle, e.g., mobile telephones, navigation aids, internet, e-services. These distracters may capture a driver's attention excessively and thus potentially increase collisions based on distraction causes.

Generally, a secondary task becomes a distraction (including visual-, auditory-, mental-, cognitive-, and biomechanical distraction) when the driver's attention is captured by information that is irrelevant to the driving situation to the degree that:

(a) insufficient attention is left for the primary control task of driving, and/or (b) driving performance (e.g., lane keeping or speed control) and safety are compromised.

Finally, workload refers to how busy a driver is and the amount of effort the driver needs to perform the tasks at hand. Having a lot to do ("high workload") creates much to attend to (i.e., a high perceptual demand) and much to act upon (i.e., a high action demand). For example, driver workload increases both with the primary driving task demand (caused e.g., by road and environment conditions, traffic, driving style, etc.) as well as with the execution of secondary tasks (distraction) mentioned above. Thus, high workload situations increase the probability of drivers becoming distracted.

WO 01/60254 A1 discloses a method and means for monitoring driver alertness by imparting an impulse to the steering or some other part of the vehicle with which the driver actively interacts, whilst underway, by means of one or more actuators. The spontaneous reaction of the driver to this impulse is detected by one or more sensors and is compared with the impulse itself in order to draw conclusions regarding the driver's presence of mind. However, imparting an impulse to any part of the vehicle is considered as detrimental. Furthermore, the driver's alertness cannot be monitored continuously but only at such a moment in which the impulse is imparted.

Another approach to the determination of driver alertness is a "Driver alertness indication system" (DAISY) of Spericon Ltd. as disclosed in the article "Principles of operation and system feasibility" dated June 2002. By this system, the accumulated action of external forces exerted on the vehicle and disturbing the movement of the vehicle along its path is detected, and the action of the driver who acts to maintain the vehicle on the road is analysed. The analysis of the driving pattern the pattern of the disturbances allows a continuous determination of the driver level of alertness. However, the necessary separation between the movements initiated by the driver (which originate at the steering wheel) and the movements due to the external disturbances (which originate at the road wheel) has to be evaluated in consideration of the free play and the time lag in the steering system of the vehicle so that an intensive use of mathematical and engineering techniques as well as the application of complex algorithms is required.

U.S. Pat. No. 5,691,693 discloses an "Impaired transportation vehicle operator system" and a related method in which the head position and head movement of the driver is sensed by means of three capacitive coupling sensors. The output signals of the sensors are analyzed by a microprocessor which records, tracks and compares the operator head movement data with stored profiles of normal head movement and profiles of impaired head movement to detect any head movement indicative of operator impairment. However, this system and method is not able to detect and quantify what types of head movement are part of the normal and are part of the impaired profiles.

It is an object of the invention to provide a method and system for detecting or recognizing impairment and/or inattention (especially caused by drowsiness, distraction and/or workload) of a person e.g., when monitoring a process, e.g., a vehicle driver when driving a vehicle, which might lead to reduced safety of driving.

It is another object of the invention to provide a method and system for quantifying the level of impairment and/or inattention of a person, especially a vehicle driver.

Furthermore, it is an object of the invention to provide a method and system for detecting or recognizing impairment and/or inattention for quantifying the level of impairment and/or inattention of a person, especially a vehicle driver, on the basis of head movement patterns.

These objects are solved by a method according to claims 1 and 6 and by a system according to claim 14.

The subclaims disclose advantageous embodiments of the methods and system according to claims 1, 6 and 14, respectively.

BRIEF DESCRIPTION OF THE DRAWINGS

Further details, features and advantages of the invention are evident from the following description of exemplary embodiments of the invention in connection with the drawings, in which schematically shows.

DETAILED DESCRIPTION

Figure 1:
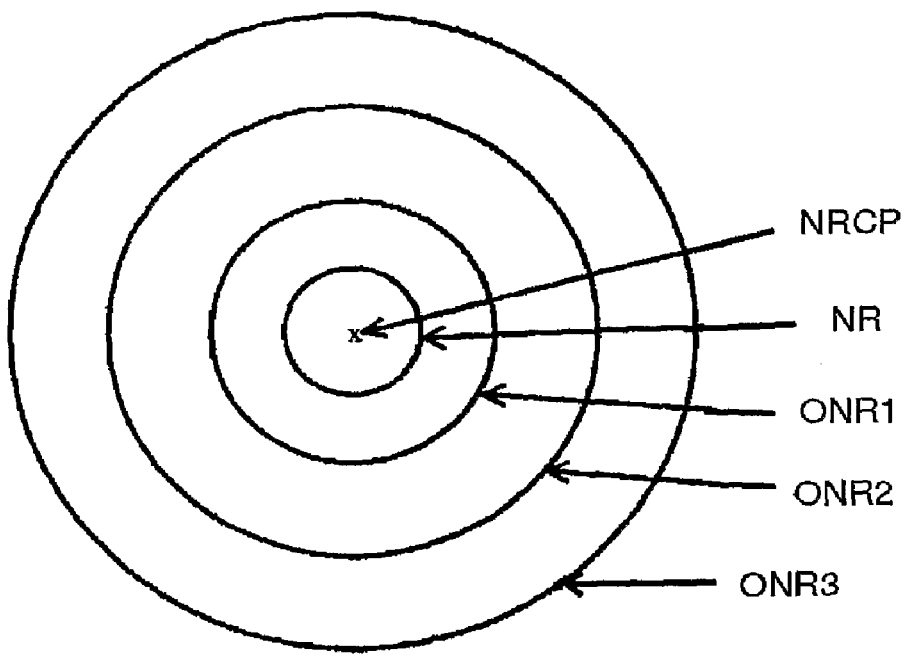
FIG. 1 a schematic view of normal regions and outside normal regions of head movements.

In the following, the invention shall first be explained in the form of preferred methods and systems for recognizing drowsiness.

The basis of this inventive methods and systems is that muscles fall into a relaxed state when a person becomes drowsy. Such drowsiness can be caused e.g., by fatigue and/or alcohol and/or drugs and/or medicine and/or intoxication etc. As a background, skeletal muscle tone results entirely from nerve impulses coming from the spinal cord. These in turn are controlled partly by impulses transmitted from the brain and partly by impulses that originate in muscle spindles located in the muscle itself. The muscle spindle impulses provide the nervous system with continuous feedback of information from each muscle, giving the status of each muscle at each instant, which is length, tension, and how rapidly length or tension of the muscle is changing. Thus, there is a general relaxing of muscle tone with drowsiness. As a result of loss of muscle tone especially in the neck and of sluggishness in reaction to disturbances, the head starts to move around more and with larger amplitudes of movements. This change of head movements can be quantified by the methods and systems according to the invention.

The following measures of drowsiness may all be used as absolute or relative values. As absolute values, the measures are taken to indicate a level of drowsiness on a scale from alert to asleep. As relative values, the measures are used to indicate the difference when comparing to a driving segment in which the driver is alert. Since head movements may differ from person to person, the method can have an initiation phase where normal or alert behaviour is recorded and/or analyzed and quantified and used for comparison. The degree of deviation from this normal or alert behaviour then indicates drowsiness.

Generally, it has to be distinguished between detecting drowsiness from head movements alone (first embodiment of the invention) and between detecting drowsiness by comparing head movements with a disturbance (second embodiment of the invention).

The first embodiment mentioned in the preceding paragraph shall now be explained in more details.

The head movement is generally decribed by three head rotation components (Pitch, Yaw and Roll), and three head translation components according to a Cartesian coordinate system with the axis x, y and z (Posx, Posy, Posz). These six components can be combined to a head movement signal HMOVE that completely describes the head movement.

Preferably, each of the six signal components is pre-processed to remove measurement noise and long term postural changes of the driver. One way to achieve this is to use a high-pass filter to remove the long term postural changes, which by nature are of low frequency, and a low-pass filter to suppress or at least attenuate the signal noise. Both can of course be achieved by an appropriate band-pass filter as well.

After this pre-processing, the global measurement of the total head movement HMOVE can e.g., be expressed and calculated as a function of the six degrees of freedom and their first- and second-degree time-dependent derivatives according to equation (1.1):

$$\text{HMOVE} = f(\text{Posx, Posy, Posz, Pitch, Yaw, Roll}, \delta/\delta t \text{ Posx}, \delta/\delta t \text{ Posy}, \delta/\delta t \text{ Posz}, \delta/\delta t \text{ Pitch}, \delta/\delta t \text{ Yaw}, \delta/\delta t \text{ Roll}, \delta^2/\delta t^2 \text{ Posx}, \delta^2/\delta t^2 \text{ Posy}, \delta^2/\delta t^2 \text{ Posz}, \delta^2/\delta t^2 \text{ Pitch}, \delta^2/\delta t^2 \text{ Yaw}, \delta^2/\delta t^2 \text{ Roll}) \quad (1.1)$$

This general function or model can be chosen and tuned differently for different applications. For example, a global head movement measure could be defined according to equation (1.2):

$$\text{HMOVE} = (A^*\text{pitch}2 + B^*\text{yaw}2 + C^*\text{roll}2 + D^*\text{Posx}2 + E^*\text{Posy}2 + F^*\text{Posz}2)^{1/2} \quad (1.2)$$

wherein A to F are weighting factors which determine the sensitivity for different types of head movements and thus the sensitivity of the measurement.

For detecting drowsiness from this head movement signal HMOVE, the inventive methods and systems are based on and make use of a (first) reference calculation of a normal region center point (NRCP) X or of a normal region (NR). Reference is made to FIG. 1 which shows such a NRCP which is surrounded by a NR. Furthermore, a first, a second and a third outer normal region ONR2, ONR3 are indicated in the form of concentric circles surrounding the NR. (Although FIG. 1 shows a two-dimensional area (e.g., pitch and yaw movements), this can be applied and extended to e.g., all six dimensions as mentioned above).

At first, the NRCP as shown in FIG. 1 is calculated for each of the head rotation and head translation signal components measured as mentioned above during the first few minutes (e.g., three minutes) of driving or the first few minutes (e.g., three minutes) of driving in a certain environment. Exemplary results of such calculations are shown in FIGS. 3 and 4.

Figure 2:
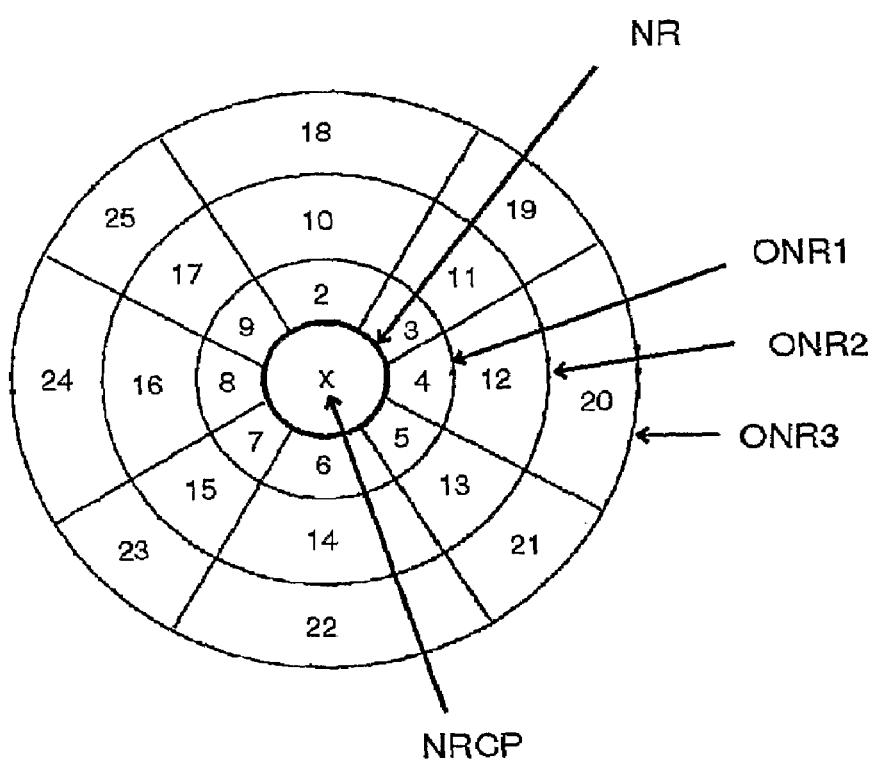
FIG. 2 a schematic view of sub-regions within the outer normal regions of head movements.
Figure 3:
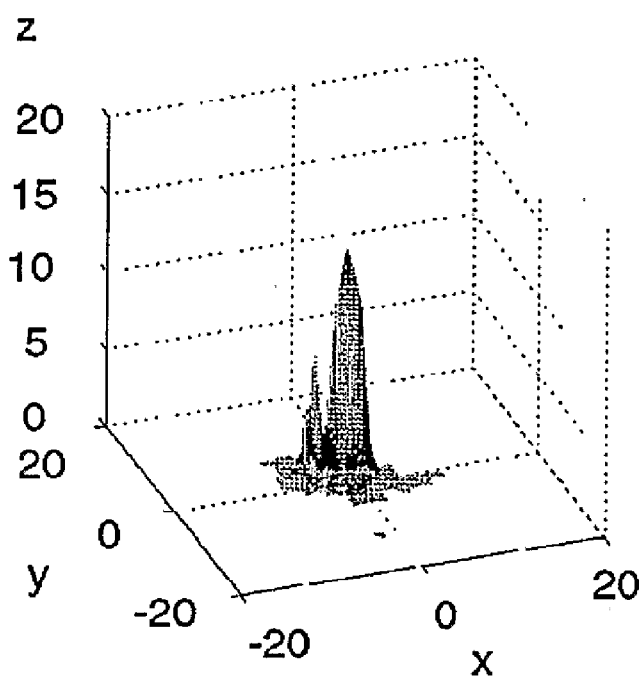
FIG. 3 a plot of the density of horizontal and vertical head rotations of alert drivers.
Figure 4:
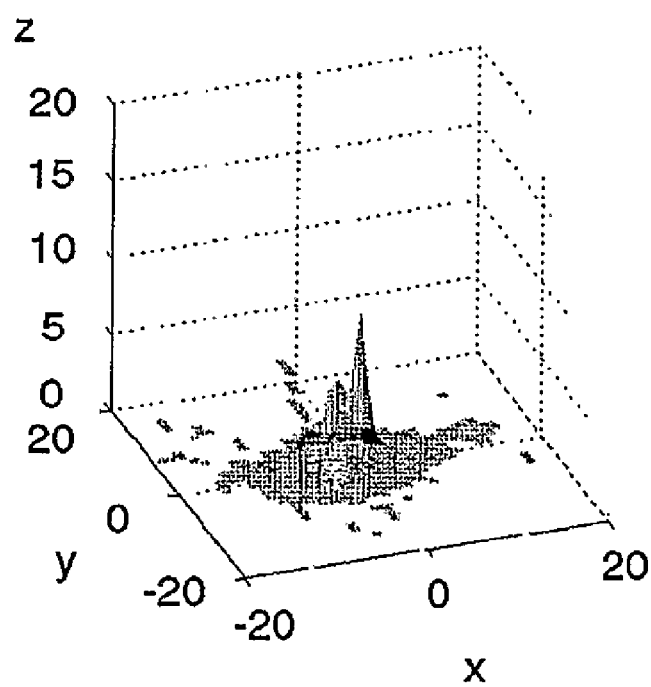
FIG. 4 a plot of the density of horizontal and vertical head rotations of drowsy drivers.

FIG. 3 shows a plot of the resulting density of signal components related to horizontal and vertical head rotations (as an example) of a plurality of alert drivers, whereas FIG. 4 shows this density for a plurality of drowsy drivers. On the x-axis of both these Figures, signal components of vertical rotations (pitch movements of the head in degree) and on the y-axis signal components of horizontal rotations (yaw movements of the head in degree) are indicated, whereas on the z-axis the density of these movements in percent per bin or funnel is indicated. The NRCP according to FIGS. 1 and 2 corresponds with the point at values and FIG. 3 shows the result of such a first reference calculation for head rotation signals of 12 alert drivers during preferably the first three minutes of their respective driving. In comparison to this, FIG. 4 shows the result of second calculations (as explained below) for 12 drivers in case that they are drowsy.

For both alert and drowsy drivers there is a distinct peak of the density of the signal components which is considered as the NRCP (X). By comparing FIGS. 3 and 4 it is obvious that finding the NRCP does not rely on the driver being alert because the NRCP results independently of the impairment and/or inattention of the driver.

At second, it is evaluated how a change in the distribution of the density of the signal components between the different regions in FIGS. 3 and 4 could be classified as drowsiness. In order to compare a current distribution with another distribution, a basic trough for each individual driver is defined. The basic trough is established on the basis of head movements during the first few minutes of driving (or the first few minutes of driving in a particular environment). Thus, for a relative measure on the basis of the basic trough it has to be assumed that the driver is alert and not under the influence of drugs during these first few minutes of calibration. For an absolute measure, a threshold is pre-set and no calibration period is needed.

Generally, the basic trough can be defined either on the basis of a plurality of alert drivers so that it can be used as a driver-independently standard for any driver, or the basic trough is established individually for each specific (alert) driver who is monitored by the related system. The sensor used for these measurements is e.g., a head-and eye-tracker based on one or two cameras and a computer software for processing the output signals of the camera (s). The sensor especially measures head position and direction in three-dimensional coordinates. Of course, other measurement techniques or other sensors (e.g., infrared sensors) can be used as well.

In order to calculate the distribution of head movements within each region (NRCP and each NR and ONR e.g., according to FIG. 1), each signal component (in each head movement signal) is counted in its corresponding region. The more signal components (e.g., and Posy) are inside one region, the higher the value will be for this region and the lower for the other regions (all regions sum up to 100% for each head movement signal). If the regions of FIG. 1 are laid into the x/y-plane of FIGS. 3 and 4 they will indicate the amount of horizontal and vertical head movements within each of the regions (most movements are in the normal region NR) for these two signal components. From FIGS. 3 and 4 it is obvious as well that the distribution between the regions differs considerably for alert and drowsy drivers.

The regions have the form of a grid (rectangular, circular according to FIGS. 3 and 4, or they have another shape) of and the distribution is a normalized histogram for the signal components based on the sizes of the For example it is assumed that for a particular signal component a first region between 0 and 1, a second region between 1 and 2 and a third region between 2 and 3 is defined and five samples of the signal component having values of 0,5; 1,1; 2,4; 0,9 and 0,3 are considered. The resulting distribution would be 60% of the values within region 1 and each 20% in region 2 and 3, respectively. However, according to the invention there are up to six-dimensional which are evaluated in this way and it is assumed that certain "shapes" of these distributions indicate drowsiness.

For each head rotation and head translation signal component, each sample is added to a related (rotation- and translation-) funnel wherein a funnel size of e.g., 0.98 by 0.98 degrees (128×128 for +/−30 degrees from straight ahead, or the zero point) can be used. Then, the mode of each funnel (samples with the largest frequency in a funnel) is set as a normal region center point (NRCP) X for each rotation and translation signal components, respectively, and stored.

Subsequently, the above first (reference) calculation (by which the NRCP or the NR has been calculated) is repeated preferably periodically with a predetermined time distance as a plurality of second calculations. Each result of the subsequent second calculations is compared with the first calculation. If the difference between both exceeds a predetermined value, it is supposed that the driver is drowsy and a signal is output or an alarm device is activated. It is noted that it is the distribution which is continuously calculated. For this purpose a sliding time window is used that allows to focus e.g., on the past minute or another time interval of driving and disregard what happened before this time interval. The continuously calculated distribution is then compared to the reference distribution (or a pre-defined "alert"-distribution). When the difference exceeds a predefined threshold value or when the continuously calculated distribution is deviating from a predefined reference shape or has a certain predefined shape it is assumed that the driver is drowsy.

In this disclosure, a "sliding time window" is a window which is sliding along a signal. As a new sample is added, the oldest sample in the time window will be deleted. All measurements are calculated based on the samples within the sliding time window.

As shown in FIG. 2, the outer normal regions ONR1, ONR2, ONR3 can be further divided into sub-regions 2 to 9,10 to 17, and 18 to 25, respectively (region 1 is considered as the normal region NR). By this, the number of funnels/bins and their shape and size can be different from the division shown in FIG. 1. This might be advantageous for evaluating and comparing certain distributions with respect to certain signal components (e.g., in the case of FIGS. 3 and 4 with respect to the horizontal and vertical head rotations).

For evaluating a percentage normal region (PNR) measure, at first each sample within a sliding time window (e.g., a one minute time window with a 60 Hz update frequency) is classified as being either i.e., lying within a normal region (NR) or a "0", i.e., lying outside the normal region (ONR) on the basis of a normal region criteria. The normal region criteria is, for example, calculated by taking the distance from normal region center point X and setting a cutoff threshold, e.g., 5 degrees for rotational position of the head and/or 5 cm for translational position of the head as a radius around the normal region center point X, indicating e.g., a first normal region NR as indicated in FIG. 1. Of course several normal region criteria with different thresholds can be established leading to a second normal region NR2, a third normal region NR3, a fourth normal value.

The cutoff threshold (s) could for example also be defined as data within one standard deviation from normal region center point X, or elsewise identified by clustering algorithms, thereby allowing normal region (s) NR to be non-circular as well.

Again, those samples that fall within the cutoff threshold are classified as "within the related normal region (NR)" and those that fall outside are classified as "outside the related normal region (ONR)".

In the next step, a calculation of percentage is made by dividing the number of datapoints within the related normal region NR by the total number of data-points within the time window and e.g., multiplying the product by 100 so that a percentage normal region measure (PNR) is achieved.

Besides the percentage normal region measure (PNR), a Standard Deviation of distance to normal region center point (SD_DNRC) from mode road center (SD-MRC)—can be calculated in the same time window as mentioned above, according to the standard deviation formula, with the exception that the mean value is replaced by mode:

More in detail, the standard deviation (SD) of the distance between the NRCP and the current signal value (called DNRC) is calculated. However, the usual mean value used in the has to be replaced with the mode i.e., the NRCP. The calculation is performed on the limited amount of data contained within a sliding time window. Thus it becomes a RMS (Root Mean Square) of the DNRC. A threshold at e.g., two times the SD of an alert driver is set, and when the threshold is reached or exceeded, it its assumed that the driver is drowsy:

$$DNRC = ((HMOVE - NRCP)2)^{1/2} \; HMOVE, NRCP \; \epsilon^{RN} \quad (1.3)$$

$$SD\_DNRC = (\Sigma DNRC2/WindowLength)^{1/2} DNRC \; \epsilon_R \quad (1.4)$$

RN in formula (1.3) are real numbers (not complex numbers) of dimension N, wherein N=1, 2, 3, 4, 5, 6, 7, 8, . . . depending on how many signal components were used to form HMOVE and NRCP. Consequently, R (or R1) in formula (1.4) are real numbers of one dimension.

In equation (1.3), HMOVE could e.g., be defined according to formula (1.5):

$$HMOVE = (A*Posx, B*Posy, C*Posz, D*Pitch,$$
$$E*Yaw1, F*Roll) \; HMOVE \; \epsilon_{R6} \quad (1.5)$$

wherein A to F are weighting factors.

Drowsiness is then calculated based on pattern recognition (e.g., neural net or statistical) of the distribution of head movements between the normal regions NR; HR1m NR2, . . . and/or outer normal regions ONR1, ONR2, . . . and the segments 2,3, . . . 25. An alert driver will have a different distribution in the regions according to FIG. 1 or 2 compared to a drowsy driver.

In more details, for each instant in time and for each driver there will be a unique distribution of head movements in the different regions NR, ONR. Each distribution indicates how the driver has moved his head during the past X minutes (depending on the length of the sliding time window). It is assumed that the distributions of drowsy drivers differ considerably from alert drivers (again, see FIGS. 3 and 4). In order to classify a driver as having the distribution of a drowsy driver, pattern recognition methods are used. According to FIG. 4 the drowsy drivers have a much more smeared out distribution of the density of the signal components compared to the alert drivers according to FIG. 3.

In a very simple example, drowsiness could be defined as having a predefined value X % of the head movements outside a predefined circle (which in FIGS. 3 and 4 is placed in the x/y-plane). However, FIGS. 3 and 4 only show two dimensions, but the distribution and recognition can be done in N-dimensions (signal components), analyzing e.g., both head position and head rotation, as well as velocity or angular velocity of the head movement.

Figure 5:
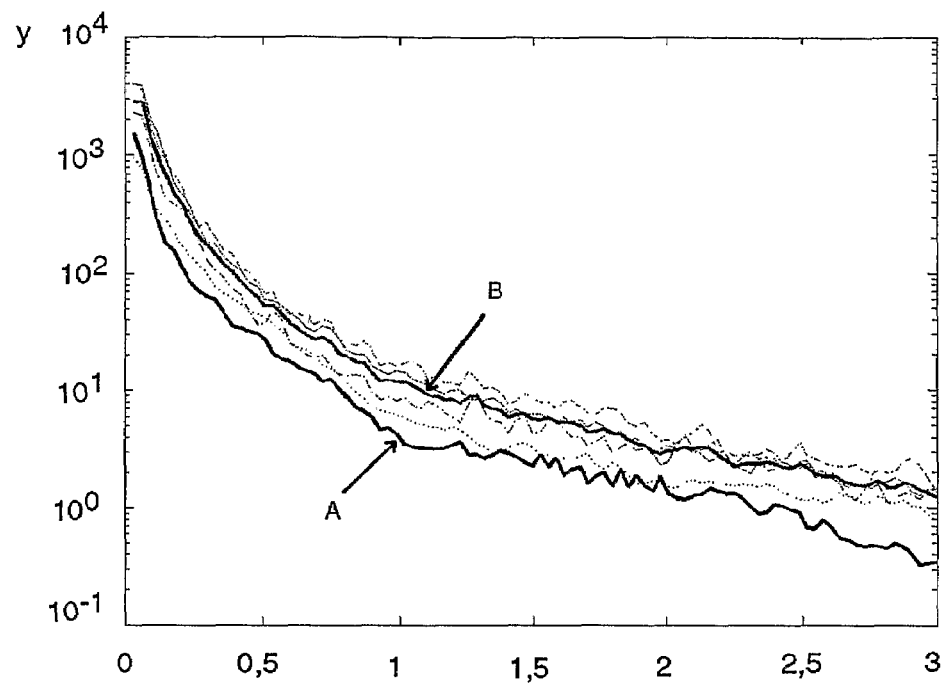
FIG. 5 a first power spectral density plot of vertical head rotations of alert drivers in comparison to drowsy drivers.

FIG. 5 shows a plot of the power spectral density (indicated on the y-axis) of vertical head rotations (pitch movements) of drowsy drivers (curve B) in comparison to alert drivers (curve A) in terms of the frequency in Hertz (indicated on the x-axis).

Figure 6:
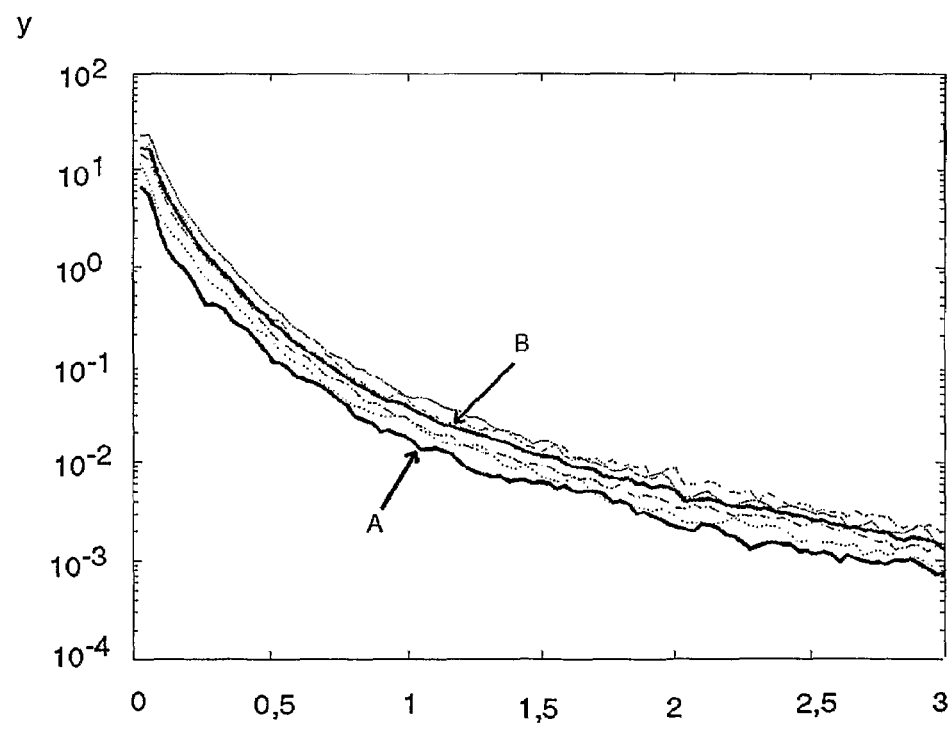
FIG. 6 a second power spectral density plot of vertical head positions of alert drivers in comparison to drowsy drivers.
Figure 7:
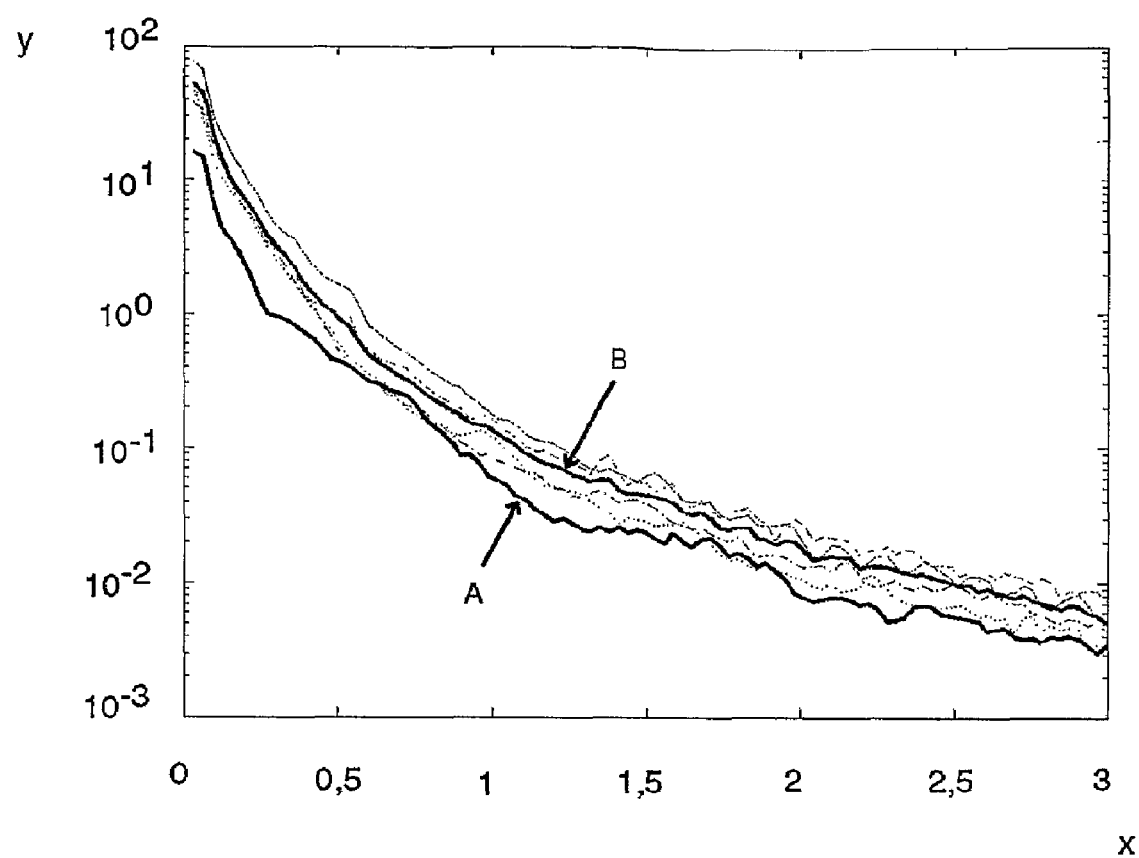
FIG. 7 a third power spectral density plot of the horizontal (depth of) head positions of alert drivers in comparison to drowsy drivers.

FIG. 6 shows such a plot of the power spectral density for vertical head positions (translation movement) of drowsy drivers (curve B) in comparison to alert drivers (curve A) whereas FIG. 7 shows such a plot of the power spectral density for horizontal (depth of) head positions (translation movement), preferably comprising movement-components in a back-forward direction, again of drowsy drivers (curve B) in comparison to alert drivers (curve A). The y-axis in FIGS. 6 and 7 is again denoted with the power spectral density and the x-axis of FIGS. 5 and 6 is denoted with the frequency in Hertz.

FIGS. 5 to 7 show a general increase in head movements of drowsy drivers. More in detail, curve A represents the frequency content of head movements of 12 alert drivers driving for 20 minutes each. In FIGS. 5 to 7 the alert drivers show less head movements across all frequencies.

The drowsy driver data have been measured in blocks of 20 minutes each (e.g., drowsy block (DB) 1 represents the first 20 min of all 12 drowsy drivers, drowsy block (DB) 2 represents the second 20 min, etc). The trend in data from such DB 1 to a DB 4 (which in this example begins 40 minutes after the end of DB 1 and lasts for 20 minutes) shows that the drowsy drivers are effected by time-on-task. It has been measured that there is a general increase in head movements from DB1 to because drivers are driving accordingly longer. This trend, however, is reversed sometimes in that the DB4 has a level slightly below but yet above DB2. The reason for this could be that the drivers expect that the trip would be ending and thus became slightly more alert towards the end of the trip. The curves B in FIGS. 5 to 7 represent the power spectral density curves as a sum of all such drowsiness blocks 1 to 4 to DB4). The curves of these drowsiness blocks to DB4 are indicated in FIGS. 5 to 7 with dashed lines.

Presenting the data in DBs provides an illustration of the trend of increasing head movements with increasing drowsiness. The indicated curves B show the power spectral density content corresponding with the same data as shown in FIGS. 3 and 4.

These power spectral density data provide a strong evidence showing that there is indeed an increase in head movements as drivers become increasingly drowsy.

Another alternative is to measure the power spectral density data on a real-time basis so that a real-time measurement of drowsiness can be conducted. For this purpose, the power spectral density data could be calculated in real-time either across the frequencies e.g., shown in FIGS. 5 to 7 or a subset of these frequencies.

The second embodiment of a method and system according to the invention is proposed for detecting drowsiness by comparing head movement reactions in case of a disturbance and shall now be explained in more details.

Generally, the drowsier a driver is the less control he has of his corrective head movement, that means in this case head movements which try to counteract a disturbance. The disturbance could be side wind, rough pavement or simply movements induced by the vehicle itself (common in trucks). A basic principle is to measure the disturbance and the corrective head movement of the driver. The difference between these signals (the disturbance and the reaction) which is the head movement reaction (HMR) measure is an estimate of how well the driver compensates for the disturbance. An alert driver has faster, more precise, and cushioned reactions whereas a drowsy driver exhibits slower, less precise and sloppy reactions with higher amplitudes of dislocalization (<<rubberneck>>). Consequently, the difference between disturbance and reaction is greater for drowsy drivers.

First, the disturbance itself has to be measured. This could be done in a number of ways (or combinations of these) like e.g., the following:

Measuring dynamic properties of objects in a camera view, for example body movements or loose objects relative to the background;

Measuring the force acting on the driver with an acceleration sensor (for example placed in the seat);

Measuring the cabin air-suspension and tilt angle compared to the rest of the truck;

Measuring steering wheel movements.

The reactions to the disturbances are contained in head movements (head movemovement reactions (HMR) to disturbances can be identified and filtered out in a number of ways as for example:

A threshold trigger can be set on the disturbance signal. Reactions are only calculated for disturbances which are larger than a certain threshold. Thus, the measurement is probe based (the probe being the disturbance) and not a continuous signal;

Head movements could only be used if the vehicle is travelling fairly straight for a predefined period of time and above a predefined speed threshold, i.e., not while turning onto a new road, going around a roundabout or while in a city;

Head movements should be ignored when signalling to change lanes.

Finally, the combination of GPS- and map-matching data and/or statistical pattern recognition data can be used to define the environment and to evaluate whether the vehicle is travelling or is going to travel fairly straight and when disturbances can be used or have to be used and when not.

As mentioned above, the HMR measure is a function of disturbance and reaction:

$$HMR = (Distubance, Reaction) \quad (2.1)$$

The disturbance is a force acting on the driver and the reaction is the response reaction of the driver with respect to his head movements. The HMR function could for example be defined to be:

The difference (e.g., with respect to displacement) between the reaction and the normal region center point (NRCP) X. The difference is larger for drowsy drivers than for alert drivers;

The RMS (root mean square) value of the difference between the reaction and the normal region center point X. Again, a low RMS value indicates that head movement is being controlled well and the driver is alert. A high RMS value indicates a drowsy driver;

Pattern recognition of HMR;

The error between a reference model for a head movement in response to a disturbance and the measured head movement in response to the same disturbance. The error represents the amount of drowsiness. The alert driver head movement response to disturbances could for example be a physical model of a particle mass on top of two rods connected with an upper joint and a lower joint at the bottom, which is a simple model of the head and spine. The lower joint represents the seat contact with the driver, the lower rod represents the body trunk, the upper joint represents the neck, and the particle mass represents the head. Disturbances in the driver environment (truck cab) are measured and fed into the model which result in modelled head movements, which are then compared with measured head movements. The model is tuned to react as the driver when she/he is alert. Models such as those of crash test dummies could be used.

According to a third embodiment of a method and system according to the invention, distraction of the driver can be recognised by applying the above methods in the following way:

Especially in a truck, a bus, a train, but even in a smaller car, interaction with integrated systems within the cab or cabin sometimes demands large eye movements (back and forth between road center and system) which are often accompanied by smaller head movements back and forth in the same direction. This is also true for side mirror checks and over the shoulder checks. These head movements could be identified and classified as distractive tasks and detected and evaluated as explained above.

According to a fourth embodiment of a method and system according to the invention, workload of the driver can be recognised by applying the above methods considering the fact that workload can be quantified in terms of the amount of head movement. The following two equations exemplify this:

$$SD(HMOVE) \quad (4.1)$$

$$RMS(\delta/\delta t(HMOVE)) \quad (4.2)$$

SD stands for standard deviation, RMS for the root mean square and HMOVE can be defined as exemplified in equation (1.2).

Equations (4.1) and (4.2) are calculated over a sliding time window of a few (e.g., 4) seconds. These measures produce a continuous quantification of workload. A threshold can be used to obtain preferably a Boolean value, i.e., high or low workload, and a high-to-low workload delay is used to prevent flickering of the value. The use of high weighting factors for the absolute values (equation 1.1) makes the estimation more sensitive to simultaneous changes in several of the terms that are used to describe head movement, for example directional movement, towards the center stack, which consists of both pitch and yaw movements, and less sensitive to head movements caused by the road curvature, which are mainly yaw movements. The dynamics of the signal can be tuned by adjusting the length of the time window and/or the magnitude of the weighting factors. Instead of one threshold and a Boolean value, a plurality of thresholds could be used to obtain several levels of workload accordingly.

The time-dependent derivatives of head position and head rotation could also be used in a similar way to detect workload. For example, fast head movements would indicate a higher workload than slow head movements.

The invention is not only applicable to vehicle drivers but also to airplane pilots, air traffic controllers, engine drivers or any persons who have to be aware of not falling asleep and sit fairly still and look most of her time in the same direction.

All of the measures described in this disclosure can be individualized by saving individual specific data (e.g., distributions of densities of certain head movement signal components for an alert condition) on a driver identification chip, for example a smart card.

Figure 8:
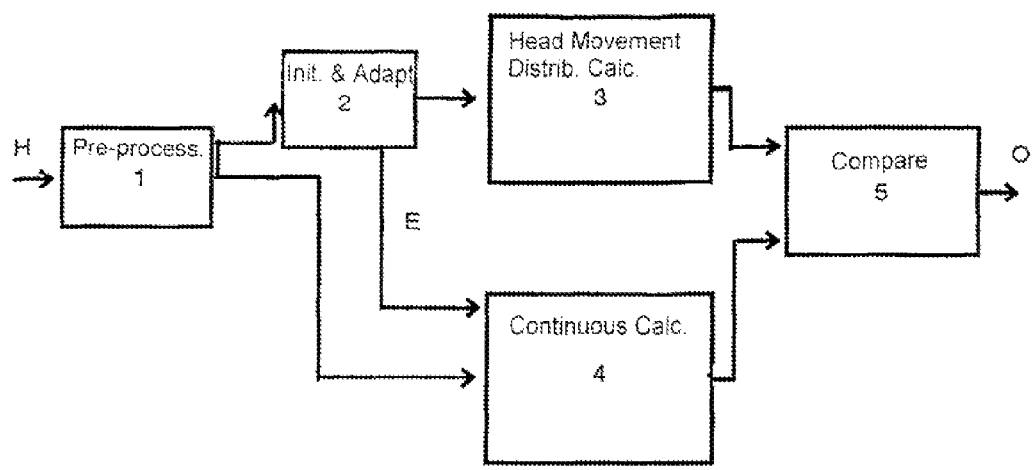
FIG. 8 a schematic flow chart of a first embodiment of a method according to the invention.

FIG. 8 shows a schematic flow chart of the first embodiment of the method according to the invention for detecting drowsiness simply by comparing an alert distribution of signal-densities (or a pre-stored distribution of such densities) with a current distribution of the related signal-densities of head movements.

The components in FIG. 8 are denoted as follows:

Arrow H: Input of driver head movement signals (all six components as mentioned above);

1: Pre-processing stage including noise suppression and removal of postural effects;

2: Initialization and adaptation block for initializing the system parameters that are specific to the driver (this may include a continuous adaptation as well);

3: Head movement distribution calculation for the alert initialization period (or adaptation of the pre-defined head movement distribution of the alert driver). This step is paused after a predefined period of time and serves then as a the reference distribution for an alert driver;

Arrow E: Enables the drowsiness calculation when initialization has been finished;

4: Continuous calculation of head movement signal distributions based on the preprocessed head movement signals of the driver delivered by component 1 for the last predefined X minutes of driving ("sliding time window");

5: Comparing the current head movement signal distribution with the head movement signal distribution of the alert driver. This component contains the criterias and/or thresholds for when the driver is to be considered drowsy;

Arrow O: Output of continuous or discrete drowsiness values.

Figure 9:
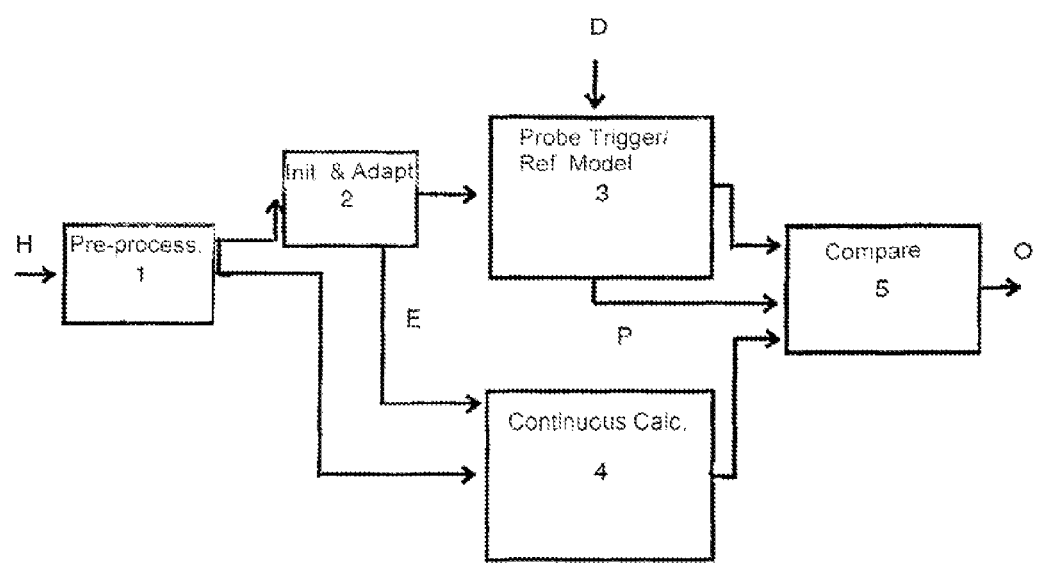
FIG. 9 a schematic flow chart of a second embodiment of a method according to the invention.

FIG. 9 shows a schematic flow chart of the second embodiment of the method according to the invention for detecting drowsiness by comparing head movement reactions in case of a disturbance.

The components in FIG. 9 are denoted as follows:

Arrow H: Input of driver head movement signals (all six components as mentioned above);

1: Pre-processing stage including noise suppression and removal of postural effects;

2: Initialization and adaptation block for initializing the system parameters that are specific to the driver (this may include a continuous adaptation as well);

Arrow E: Enables the drowsiness calculation when initialization has been finished;

Arrow D: Input of a disturbance signal (e.g., accelerometer signal);

3: Probe trigger and/or simple reference model of the driver. It is decided which disturbances are large enough (and exceed a predefined value) to be used and which are feed through to the comparison component 5. The component 3 includes a simple reference model of the driver (e.g., the mechanical model described above) as well. Disturbances D are fed into the model and the output (simulated head movements) is then fed through to the comparison component 5;

Arrow P: Trigger signal, indicates when to compare and/or calculate measures;

4: Continuous calculation of head movement measures (including head movement distribution) for the last predefined X minutes of driving;

5: Comparing the current head movement measures with the modelled head movement distribution. This component contains the criterias and/or thresholds for when the driver is to be considered drowsy based on this comparison and the values of head movement-and disturbance measures;

Arrow O: Output of continuous or discrete drowsiness values.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed is:

1. Method for recognizing and/or detecting impairment and/or inattention of a person by detecting and evaluating head movements of the person on the basis of at least one component, the at least one component being at east one of three head rotation components, pitch, yaw, roll, and three head translation components, each in one of three orthogonal directions, the method comprising the following steps:

calculating within at least one predetermined time interval an actual density pattern of the at least one component in a form of an actual distribution of numbers of samples of the at least one component between at least one of a normal region and a normal region center point, which includes a peak of the density pattern, and a plurality of pre-set outer normal regions surrounding the at least one of the normal region and normal region center point;

comparing the actual density pattern with a reference density pattern of the at least one component in a form of a reference distribution of samples of the at least one component in the at least one of the normal region and normal region center point; and evaluating a difference between at least one one of actual and reference patterns and actual and reference distributions and outputting a signal if the difference exceeds a predetermined value.

2. Method according to claim 1, wherein the reference density pattern is evaluated during at least one predetermined time interval in which the person has a reference level of impairment and/or inattention.

3. Method according to claim 1, wherein the reference density pattern is provided in a form of at least one threshold distribution which is pre-defined independently from the person as a standard for any person.

4. Method according to claim 1, wherein the regions have a form of a end of one of bins and funnels and the distribution is a normalized histogram of the signal components based on sizes of the one of the bins and funnels.

5. Method according to claim 1, wherein the at least one predetermined time interval is a sliding time window and wherein the actual density pattern of the at least one component is continuously calculated based on the samples within the sliding time window.

6. Method according to claim 1, wherein at least one threshold is predetermined for defining at least one normal region, respectively.

7. Method according, to claim 6, wherein the at least one threshold is determined with respect to a standard deviation from the normal region center point.

8. Method according to claim 6, wherein comparing the actual density pattern with the reference density pattern includes evaluating a difference between both the actual density pattern and the reference density pattern in at least one of different normal regions and segments of at least one normal region.

9. Method according to claim 1, comprising recognizing and/or detecting workload of a person by detecting and evaluating head movements of the person based on at least one of an amount and the time dependent derivative of at least one of three head rotation components and three head translation components.

10. System for conducting, a method according to claim 1.

11. A computer medium that contains a program comprising computer program code means adapted to perform a method according to claim 1 when the program is run on a programmable microcomputer.

12. A computer medium that contains a program according to claim 11 adapted to be downloaded to a system when run on a computer which is connected to the internet, the system being adapted to perform a method for recognizing and/or detecting impairment and/or inattention of a person by detecting at and evaluating head movements of the person on the basis of at least one component, the at least one component being at least one of three head rotation components, pitch, yaw, roll, and three head translation components, each in one of three orthogonal directions, the method comprising the following steps:

calculating within at least one predetermined time interval an actual density pattern of the at least one component in a form of an actual distribution of numbers of samples of the at least one component between at least one of a normal region and a normal region center point, which includes a peak of the density pattern, and a plurality of pre-set outer normal regions surrounding the at least one of the normal region and normal region center point;

comparing the actual density pattern with a reference density pattern of the at least one component in a form of a reference distributions of samples of the at least one component in the at least one of the normal region and normal region center point; and evaluating difference between at least one one of actual and reference patterns and actual and reference distributions and outputting a signal if the difference exceeds a predetermined value.

13. A computer medium that contains a program as set forth in claim 11, wherein the program is stored on a computer usable medium.

14. Method for recognizing and/or detecting impairment and/or inattention of a person who is at least one of actively and reactively connected with an object, wherein the object is at least one of influenced and affected by an external disturbance which causes a head movement reaction of the person, comprising the following steps:

detecting the disturbance exerted onto the object by external forces;

detecting head movement reaction of the person upon the disturbance based on at least one component, the at least one component being at least one of three head rotation components and three head translation components;

evaluating a difference between the head movement reaction and at least one of a predefined reference head movement reaction and a stored previous head movement reaction upon a previous disturbance; and outputting a disturbance signal if the difference exceeds a predefined value.

15. Method according to claim 14, wherein the object is a vehicle and wherein detecting the disturbance includes measuring of at least one of the following values:

dynamic properties of objects within the vehicle;
an acceleration force acting on the person;
cabin air-suspension and tilt angle compared to a rest of the vehicle; and
steering wheel movements.

16. Method according to claim 14, wherein detecting the head movement reaction includes at least one of the following measures and evaluations:

pre-defining a threshold value for the disturbance signal and evaluating head movement reactions if the disturbance exceeds the threshold value;

evaluating head movements if the vehicle is travelling substantially in a straight direction for substantially at least one of a predefined period of time and above a predefined speed threshold value; and ignoring head movements if the vehicle is not travelling substantially in a straight direction for substantially the at least one of the predefined period of time and at above the predefined speed threshold value.

17. Method according to claim 16, wherein whether the vehicle travels substantially in a straight direction is evaluated based on a navigation/localization system and data.

18. Method according to claim 17, wherein whether the vehicle travels substantially in a straight direction is evaluated based on GPS- and map-matching data.

19. Method according to claim 16, wherein speed of the vehicle is evaluated based on a navigation/localization system and data.

20. Method according to claim 19, wherein speed of the vehicle is evaluated based on GPS- and map-matching data.

21. Method according to claim 16, wherein detecting head movement reaction is at least one of activated and deactivated based on a navigation/localization system and data.

22. Method according to claim 21, wherein detecting head movement reaction is at least one of activated and deactivated based on GPS- and map-matching data.

23. Method according to claim 14, wherein evaluation of the difference includes at least one of the following measures:

a difference between the reaction and the normal region center point;

a RMS (root mean square) value of a difference between the reaction and the normal region center point; and an error between a model for a head movement in response to a disturbance and the measured head movement in response to the same disturbance.

24. Method according to claim 14, comprising recognizing and/or detecting workload of a person by detecting and evaluating head movements of the person based on at least one of an amount and the time dependent derivative of at least one of three head rotation components and three head translation components.

25. System for conducting a method according to claim 14.

26. Method for recognizing and/or detecting impairment and/or inattention of a person based on a workload of the person by detecting and evaluating head movements of the person based on at least one of an amount and the time-dependent derivative of at least one component, the at least one component being at least one of three head rotation components and three head translation components, comprising the following steps:

calculating a standard deviation and at least one of a root mean square value of the at least one component and a root mean square value of a time dependent derivative of the at least one component over a sliding time interval for producing a continuous quantification of workload, and comparing the quantified workload with at least one threshold and outputting a signal if the difference exceeds the at least one of the threshold.

27. System for conducting a method according to claim 26.

28. Method according to claim 26, for recognizing and/or detecting distraction of the person on the basis the quantified workload.

29. Method according to claim 26, wherein the person in a driver of a vehicle.

30. Computer medium comprising computer program code means adapted to perform a method according to claim 26 when the program is run on a programmable microcomputer.

31. Computer medium according to claim 30, wherein the program is adapted to be downloaded to a system when run on a computer which is connected to the internet, the system being adapted to perform a method for recognizing and/or detecting impairment and/or inattention of a person by detecting and evaluating head movements of the person on the basis of at least one component, the at least one component being at least one of three head rotation components, pitch, yaw, roll, and three head translation components, each in one of three orthogonal directions, the method comprising the following steps:

calculating within at least one predetermined time interval an actual density pattern of the at least one component in a form of an actual distribution of numbers of samples of the at least one component between at least one of a normal region and a normal region center point, which includes a peak of the density pattern, and a plurality of pre-set outer normal regions surrounding the at least one of the normal region and normal region center point;

comparing the actual density pattern with a reference density pattern of the at least one component in a form of a reference distribution of samples of the at least one component in the at least one of the normal region and normal region center point; and evaluating a difference between at least one one of actual and reference patterns and actual and reference distributions and outputting a signal if the difference exceeds a predetermined value.

32. A computer medium that contains a program as set forth in claim 30, wherein the program is stored on a computer usable medium.

* * * * *